US012687487B2

(12) United States Patent
He et al.

(10) Patent No.: US 12,687,487 B2
(45) Date of Patent: Jul. 21, 2026

(54) METHOD AND SYSTEM FOR AUTOMATICALLY DETECTING NITROGEN CONTENT, ELECTRONIC DEVICE AND MEDIUM

(71) Applicants: Hainan Institute of Zhejiang University, Sanya City (CN); Zhejiang University, Hangzhou City (CN)

(72) Inventors: Yong He, Sanya City (CN); Xuping Feng, Hangzhou City (CN); Zhenyu Huang, Hangzhou City (CN); Ningyuan Yang, Hangzhou City (CN); Pengcheng Nie, Sanya City (CN); Haiyan Cen, Sanya City (CN); Shuiguang Deng, Sanya City (CN); Chongde Sun, Sanya City (CN); Cui Sun, Sanya City (CN)

(73) Assignees: Hainan Institute of Zhejiang University, Sanya City (CN); Zhejiang University, Hangzhou City (CN)

( * ) Notice: Subject to any disclaimer, the term of this patent is extended or adjusted under 35 U.S.C. 154(b) by 250 days.

(21) Appl. No.: 18/743,954

(22) Filed: Jun. 14, 2024

(65) Prior Publication Data

US 2024/0393235 A1    Nov. 28, 2024

(30) Foreign Application Priority Data

May 22, 2023    (CN) .......................... 202310572530.2

(51) Int. Cl.
  *G01N 21/31*    (2006.01)
  *G01N 21/84*    (2006.01)
  (Continued)

(52) U.S. Cl.
  CPC ............. *G01N 21/31* (2013.01); *G01N 21/84* (2013.01); *G01N 33/0098* (2013.01);
  (Continued)

(58) Field of Classification Search
  CPC .... G01N 21/31; G01N 21/84; G01N 33/0098; G01N 2021/8466; G01N 21/25;
  (Continued)

(56) References Cited

U.S. PATENT DOCUMENTS

2018/0035605 A1*    2/2018  Guan ................. G06V 10/7715

OTHER PUBLICATIONS

Baohua Yang et al., "Estimation of Leaf Nitrogen Content in Wheat Based on Fusion of Spectral Features and Deep Features from Near Infrared Hyperspectral Imager", Sensors 2021,21,613, pub. 2021, (Year: 2021).*

* cited by examiner

*Primary Examiner* — Mekonen T Bekele
(74) *Attorney, Agent, or Firm* — Suiter Swantz IP

(57)    ABSTRACT

A method and a system for automatically detecting nitrogen content, an electronic device and a medium are provided and relate to the field of nitrogen content detection. The method includes: selecting an optimal nitrogen content prediction model from a prediction model base according to a variety and a growth stage of a target crop to obtain a target model; detecting, based on a spectral image of the target crop, a nitrogen content of the target crop by using the target model to obtain a predicted value of the nitrogen content. The optimal nitrogen content prediction model is the model with best performance among a first nitrogen content prediction model constructed based on a hyperspectral vegetation index, a second nitrogen content prediction model constructed based on a sensitive band, and a third nitrogen content prediction model constructed based on a machine learning method.

20 Claims, 1 Drawing Sheet

(51) Int. Cl.

| | |
|---|---|
| *G01N 33/00* | (2006.01) |
| *G06V 10/58* | (2022.01) |
| *G06V 10/774* | (2022.01) |
| *G06V 20/10* | (2022.01) |

(52) U.S. Cl.
CPC ............ *G06V 10/58* (2022.01); *G06V 10/774*
(2022.01); *G06V 20/188* (2022.01); *G06V*
*20/194* (2022.01); *G01N 2021/8466* (2013.01)

(58) Field of Classification Search
CPC .... G06V 10/58; G06V 10/774; G06V 20/188;
G06V 20/194; G06N 20/00
See application file for complete search history.

METHOD AND SYSTEM FOR AUTOMATICALLY DETECTING NITROGEN CONTENT, ELECTRONIC DEVICE AND MEDIUM

CROSS-REFERENCE TO RELATED APPLICATION

This patent application claims the benefit and priority of Chinese Patent Application No. 202310572530.2 filed with the China National Intellectual Property Administration on May 22, 2023, the disclosure of which is incorporated by reference herein in its entirety as part of the present application.

TECHNICAL FIELD

The present disclosure relates to the field of nitrogen content detection, in particular to a method and a system for automatically detecting nitrogen content, an electronic device and a medium.

BACKGROUND

Nitrogen is an important nutrient for plant growth, and a proper amount of nitrogen can ensure the normal growth of plants. However, the abuse of nitrogen fertilizers is very common at present, which not only hinders the normal growth of crops but also destroy the ecological environment. Therefore, it is particularly important to detect the nitrogen content.

Traditional nitrogen content detection methods include destructive detection and nondestructive detection. Common destructive detection methods include soil testing formula, chemical analysis of stems and leaves, etc. These methods are complicated in operation, high in cost, low in efficiency and will result in damage to the physiological tissues of plants. Nondestructive detection methods mainly include image processing, machine vision and chlorophyll photometry. Although these methods can realize nondestructive detection, their measurement accuracy is low. Therefore, how to quickly and accurately detect nitrogen content has become an urgent technical problem to be solved.

SUMMARY

Based on this, embodiments of the present disclosure provide a method and a system for automatically detecting nitrogen content, an electronic device and a medium, so as to detect the nitrogen content quickly and accurately.

In order to achieve the above objects, an embodiment of the present disclosure provides the following solution.

A method for automatically detecting nitrogen content, including:

acquiring a spectral image of a target crop;

selecting an optimal nitrogen content prediction model from a prediction model base according to a variety and a growth stage of the target crop to obtain a target model;

detecting, based on the spectral image of the target crop, a nitrogen content of the target crop by using the target model to obtain a predicted value of the nitrogen content of the target crop;

wherein a constructing method of the prediction model base includes:

acquiring a sample set, wherein the sample set includes:

spectral images of sample crops of different varieties in different growth stages and true values of nitrogen contents of the sample crops;

extracting hyperspectral vegetation indices of the spectral images of the sample crops, and constructing a first nitrogen content prediction model according to a correlation between the hyperspectral vegetation indices of different varieties in different growth stages and the true values of the nitrogen contents;

extracting sensitive bands of the spectral images of the sample crops, and constructing a second nitrogen content prediction model according to a correlation between the sensitive bands of different varieties in different growth stages and the true values of the nitrogen contents; wherein the sensitive bands are a characteristic bands whose correlation with the true values of the nitrogen contents is greater than a predetermined correlation value;

training a machine learning model by using the sample set to obtain a third nitrogen content prediction model;

for any variety in any growth stage, determining a model with best performance among the first nitrogen content prediction model, the second nitrogen content prediction model and the third nitrogen content prediction model as the optimal nitrogen content prediction model.

In the embodiment, the detecting, based on the spectral image of the target crop, a nitrogen content of the target crop by using the target model to obtain a predicted value of the nitrogen content of the target crop includes:

if the target model is the first nitrogen content prediction model or the second nitrogen content prediction model, inputting the variety and the growth stage of the target crop into the target model, wherein the target model outputs the predicted value of the nitrogen content of the target crop;

if the target model is the third nitrogen content prediction model, inputting the spectral image of the target crop into the target model, wherein the target model outputs the predicted value of the nitrogen content of the target crop.

In the embodiment, the acquiring a spectral image of a target crop includes:

determining a zenith angle and an azimuth angle at which the spectral image of the target crop is acquired under sunlight;

according to the zenith angle and the azimuth angle of the target crop, using an artificial light source to compensate for the sunlight in an environment where a multispectral camera is located;

with the compensation of the artificial light source, acquiring the spectral image of the target crop by using the multispectral camera.

In the embodiment, the acquiring a sample set includes:

determining the zenith angle and the azimuth angle at which a spectral image of a sample crop of each variety in each growth stage is acquired under sunlight;

according to the zenith angle and the azimuth angle of the sample crop of each variety in each growth stage, using an artificial light source to compensate for the sunlight in an environment where the multispectral camera is located;

with the compensation of the artificial light source, acquiring the spectral images of the sample crops of different varieties in different growth stages by using the multispectral camera;

measuring total nitrogen contents of the sample crops by using a Kjeldahl method in a laboratory, where the total nitrogen contents is considered as the true values of the nitrogen contents of the sample crops.

In this embodiment, the extracting hyperspectral vegetation indices of the spectral images of the sample crops includes:

performing preprocessing, including smoothing and correcting transformation, on the spectral image of the sample crop to obtain preprocessed spectral images;

determining a spectral reflectivity of each band according to the preprocessed spectral images;

performing arithmetic operation on the spectral reflectivity to obtain the hyperspectral vegetation indices; wherein the hyperspectral vegetation indices includes a double-peak canopy nitrogen index, a normalized difference vegetation index, a modified red edge simple ratio index and a relative vegetation index.

In the embodiment, the constructing a first nitrogen content prediction model according to a correlation between the hyperspectral vegetation indices of different varieties in different growth stages and the true values of the nitrogen contents includes:

for any variety in any growth stage, optimizing a central wavelength of each index in the hyperspectral vegetation indices by using a successive projections algorithm, and substituting an optimized central wavelength into a corresponding index calculation formula to calculate an index value;

performing a Pearson correlation test on the index value of each index in the hyperspectral vegetation indices and the true values of the nitrogen contents to obtain a correlation coefficient between each index value and the true values of the nitrogen contents;

selecting three index values with highest correlation coefficient from the hyperspectral vegetation indices as optimal spectral indices;

fitting a relationship between the optimal spectral indices and the true values of the nitrogen contents by using a multiple linear regression prediction method and/or a partial least square regression method to obtain the first nitrogen content prediction model of any variety in any growth stage.

In the embodiment, the extracting sensitive bands of the spectral images of the sample crops, and the constructing a second nitrogen content prediction model according to a correlation between the sensitive bands of different varieties in different growth stages and the true values of the nitrogen contents, includes:

for any variety in any growth stage, extracting a sensitive band of a spectral image of a sample crop by using a random frog leaping algorithm;

fitting a relationship between the sensitive bands and the true values of the nitrogen contents by using a multiple linear regression prediction method and/or a partial least square regression method to obtain the second nitrogen content prediction model of any variety in any growth stage.

The present disclosure further provides a system for automatically detecting nitrogen content, including:

an image acquisition module, which is configured to acquire a spectral image of a target crop;

a model selecting module, which is configured to select an optimal nitrogen content prediction model from a prediction model base according to a variety and a growth stage of the target crop to obtain a target model;

a nitrogen content predicting module, which is configured to detect, based on the spectral image of the target crop, a nitrogen content of the target crop by using the target model to obtain a predicted value of the nitrogen content of the target crop;

a model constructing module, which is configured to construct the prediction model base; where the model constructing module includes:

a sample set acquisition unit, which is configured to acquire a sample set; wherein the sample set includes: spectral images of sample crops of different varieties in different growth stages and true values of nitrogen contents of the sample crops;

a first model constructing unit, which is configured to extract hyperspectral vegetation indices of the spectral images of the sample crops, and construct a first nitrogen content prediction model according to a correlation between the hyperspectral vegetation indices of different varieties in different growth stages and the true values of the nitrogen contents;

a second model constructing unit, which is configured to extract sensitive bands of the spectral images of the sample crops, and construct a second nitrogen content prediction model according to a correlation between the sensitive bands of different varieties in different growth stages and the true values of the nitrogen contents; where the sensitive bands are a characteristic bands whose correlation with the true values of the nitrogen contents is greater than a predetermined correlation value;

a third model constructing unit, which is configured to train a machine learning model by using the sample set to obtain a third nitrogen content prediction model;

an optimal model determining unit, which is configured to, for any variety in any growth stage, determine a model with best performance among the first nitrogen content prediction model, the second nitrogen content prediction model and the third nitrogen content prediction model as the optimal nitrogen content prediction model.

The present disclosure further provides an electronic device, including a memory and a processor, wherein the memory is configured to store a computer program, and the processor runs the computer program to cause the electronic device to execute the method for automatically detecting nitrogen content described above.

The present disclosure further provides a computer-readable storage medium, in which a computer program is stored, wherein the computer program, when executed by a processor, implements the method for automatically detecting nitrogen content described above.

According to specific embodiments provided by the present disclosure, the present disclosure discloses the following technical effects.

The embodiment of the present disclosure provides a method and a system for automatically detecting nitrogen content, an electronic device and a medium. The present disclosure is implemented in a nondestructive way, and for a crop of each variety in each growth stage, the model with the best performance among a first nitrogen content prediction model constructed based on a hyperspectral vegetation index, a second nitrogen content prediction model constructed based on a sensitive band, and a third nitrogen content prediction model constructed based on a machine learning method is taken as the optimal nitrogen content prediction model. The embodiment of the present disclosure can detect the nitrogen content quickly and accurately.

BRIEF DESCRIPTION OF THE DRAWINGS

In order to explain the embodiments of the present disclosure or the technical solutions in the prior art more clearly, the drawings that need to be used in the embodiments will be briefly introduced. Obviously, the drawings in the following description are only some embodiments of the present disclosure. For those skilled in the art, other drawings can be obtained according to these drawings without creative labor.

DETAILED DESCRIPTION OF THE EMBODIMENTS

The technical solutions in the embodiments of the present disclosure will be clearly and completely described with reference to the drawings in the embodiments of the present disclosure hereinafter. Obviously, the described embodiments are only some embodiments of the present disclosure, rather than all of the embodiments. Based on the embodiment of the present disclosure, all other embodiments obtained by those skilled in the art without creative labor fall within the scope of protection of the present disclosure.

In order to make the above objects, features and advantages of the present disclosure more obvious and understandable, the present disclosure will be explained in further detail with reference to the drawings and detailed description hereinafter.

Embodiment 1

Figure 1:
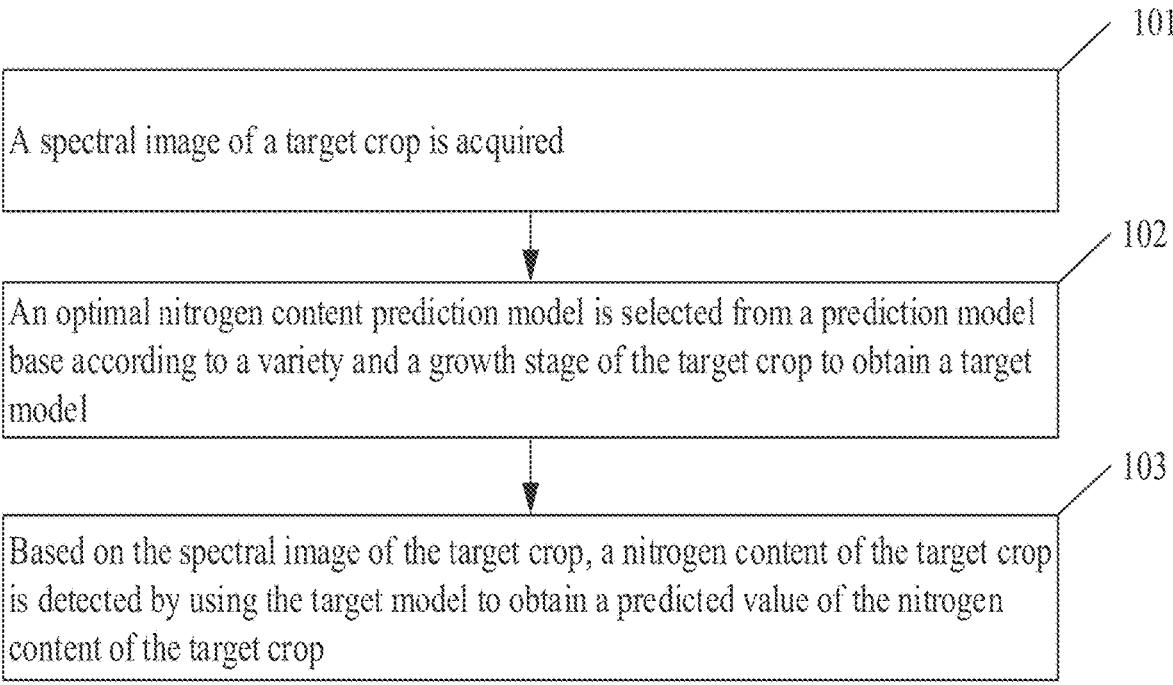
FIG. 1 is a flowchart of a method for automatically detecting nitrogen content according to an embodiment of the present disclosure.

Referring to FIG. 1, the method for automatically detecting nitrogen content in this embodiment includes Step 101 to Step 103.

In Step 101, a spectral image of a target crop is acquired.

In Step 102, an optimal nitrogen content prediction model is selected from a prediction model base according to a variety and a growth stage of the target crop to obtain a target model.

In Step 103, based on the spectral image of the target crop, a nitrogen content of the target crop is detected by using the target model to obtain a predicted value of the nitrogen content of the target crop.

In Step 102, a constructing method of the prediction model base includes the following steps.

(1) A sample set is acquired, where the sample set includes: spectral images of sample crops of different varieties in different growth stages and true values of nitrogen contents of the sample crops.

(2) Hyperspectral vegetation indices of the spectral images of the sample crops are extracted, and a first nitrogen content prediction model is constructed according to a correlation between the hyperspectral vegetation indices of different varieties in different growth stages and the true values of the nitrogen contents.

The process of extracting a hyperspectral vegetation index is specifically as follows: performing preprocessing, including smoothing and rectification transformation, on a spectral image of a sample crop to obtain a preprocessed spectral image; determining a spectral reflectivity of each band according to the preprocessed spectral image; performing arithmetic operation on the spectral reflectivity to obtain the hyperspectral vegetation index; where the hyperspectral vegetation index includes a double-peak canopy nitrogen index, a normalized difference vegetation index, a modified red edge simple ratio index and a relative vegetation index.

The process of constructing the first nitrogen content prediction model is specifically as follows:

for any variety in any growth stage, optimizing a central wavelength of each index in a hyperspectral vegetation index by using a successive projections algorithm, and substituting an optimized central wavelength into a corresponding index calculation formula to calculate an index value; performing a Pearson correlation test on the index value of each index in the hyperspectral vegetation index and the true value of the nitrogen content to obtain a correlation coefficient between each index value and the true value of the nitrogen content; selecting three index values with the highest correlation coefficient from the hyperspectral vegetation indices as optimal spectral indices; fitting a relationship between the optimal spectral indices and the true values of the nitrogen contents by using a multiple linear regression prediction method and/or a partial least square regression method to obtain the first nitrogen content prediction model of any variety in any growth stage.

In addition, there is a one-to-one correspondence among a certain growth stage of a certain variety, a hyperspectral vegetation index and a nitrogen content. In the application of actual prediction, the corresponding hyperspectral vegetation index can be acquired by inputting the corresponding growth stage of the corresponding variety into the first nitrogen content prediction model, and a corresponding predicted value of the nitrogen content can be output according to the fitting relationship between the hyperspectral vegetation indices and the nitrogen contents.

(3) A sensitive band of a spectral image of a sample crop is extracted, and a second nitrogen content prediction model is constructed according to a correlation between the sensitive bands of different varieties in different growth stages and the true values of the nitrogen contents; where a sensitive band is a characteristic band whose correlation with a true value of a nitrogen content is greater than a set correlation value.

Specifically, for any variety in any growth stage, a sensitive band of a spectral image of a sample crop is extracted by using a Shuffled Frog Leaping Algorithm (SFLA); a relationship between the sensitive bands and the true values of the nitrogen contents is fit by using a multiple linear regression prediction method and/or a partial least square regression method to obtain the second nitrogen content prediction model of any variety in any growth stage.

In addition, there is a one-to-one correspondence among a certain growth stage of a certain variety, a sensitive band and a nitrogen content. In the application of actual prediction, the corresponding sensitive band can be acquired simply by inputting a corresponding growth stage of a corresponding variety into the second nitrogen content prediction model, and a corresponding predicted value of the nitrogen content can be output according to the fitting relationship between the sensitive bands and the nitrogen contents.

(4) A machine learning model is trained by using the sample set to obtain a third nitrogen content prediction model. The machine learning model can choose a support vector machine.

(5) For any variety in any growth stage, a model with the best performance among the first nitrogen content prediction model, the second nitrogen content prediction model and the third nitrogen content prediction model is determined as an optimal nitrogen content prediction model.

Specifically, the evaluation coefficients of the first nitrogen content prediction model, the second nitrogen content prediction model and the third nitrogen content prediction model are calculated by SPSS software, and the evaluation coefficients are used to determine a modeling method to obtain a performance of a model, so as to obtain the optimal nitrogen content prediction model. The evaluation coefficients include a coefficient of determination ($R^2$) and a root mean square error coefficient (RMSE).

In one example, Step 103 specifically includes:

if the target model is the first nitrogen content prediction model or the second nitrogen content prediction model, inputting the variety and the growth stage of the target crop into the target model, where the target model outputs the predicted value of the nitrogen content of the target crop; if the target model is the third nitrogen content prediction model, inputting the spectral image of the target crop into the target model, then outputting, by the target model, the predicted value of the nitrogen content of the target crop.

In one example, Step 101 specifically includes:

determining a zenith angle and an azimuth angle at which the spectral image of the target crop is acquired under sunlight; according to the zenith angle and the azimuth angle of the target crop, using an artificial light source to compensate for the sunlight in the environment where a multispectral camera is located; with the compensation of the artificial light source, acquiring the spectral image of the target crop by using the multispectral camera. The multispectral camera may be a multispectral camera with 28 bands, and the acquired image has 28 bands.

Similarly, in the process of constructing the prediction model base, acquiring a sample set specifically includes:

determining the zenith angle and the azimuth angle at which a spectral image of a sample crop of each variety in each growth stage is acquired under sunlight; according to the zenith angle and the azimuth angle of the sample crop of each variety in each growth stage, using the artificial light source to compensate for the sunlight in the environment where the multispectral camera is located; with the compensation of the artificial light source, acquiring the spectral images of the sample crops of different varieties in different growth stages by using the multispectral camera; and measuring total nitrogen contents of the sample crops by using a Kjeldahl method in a laboratory, the total nitrogen contents being considered as the true values of the nitrogen contents of the sample crops.

In this embodiment, considering that the time of each image acquisition varies, the zenith angle and the azimuth angle under sunlight are different. In practical application, in order to ensure the stability of the image quality, a solar zenith angle and azimuth angle compensation model is established, which can detect the zenith angle and the azimuth angle of the current sunlight irradiation. The intervention of the artificial light source ensures the uniformity of the image quality to a certain extent, further improving the detection accuracy.

In practical application, a more specific implementation flow of the method for automatically detecting nitrogen content described above is as follows.

1. A spectral image of a crop is acquired. In the laboratory, the total nitrogen content of a sample is measured by the Kjeldahl method as a true value of a nitrogen content of a plant.

2. Based on an original spectrum of the crop, a hyperspectral vegetation index is extracted after a spectral transformation. The spectral transformation includes performing preprocessing, including smoothing and correcting transformation, on the original spectral data with a polynomial convolution smoothing method (SG) to filter the high-frequency noise firstly, and then calculating a first derivative of the original spectrum to eliminate the influence of baseline drift and sharpen the original spectrum contour.

After the spectral preprocessing, due to a significant interference in predicting plant nitrogen content using a single band, arithmetic operation is performed on each spectral reflectivity of each band, including a series of addition, subtraction, multiplication and division to obtain different spectral indices. Each spectral index has its own calculation formula. The calculation formula is common and will not be described in detail herein. The hyperspectral vegetation index includes a Double-peak Canopy Nitrogen Index (DCNI), a Normalized Difference Vegetation Index (NDVI), a Modified Red Edge Simple Ratio Index (mSR705) and a Ratio Vegetation Index (RVI).

3. The correlation between these indices and the nitrogen concentration or content is analyzed. The successive projections algorithm (SPA) and the random frog leaping algorithm are used to select sensitive characteristic bands, thereby obtaining an optimal central wavelength of each index, and the crop nitrogen content prediction model with an optimized spectral index is constructed, which is the first nitrogen content prediction model.

Specifically, Matlab software and Statistical Product and Service Solutions (SPSS) software are mainly used to perform a Pearson correlation test on the spectral indices obtained in the previous steps and a nitrogen content of a plant, and then three spectral indexes with the highest correlation are selected after calculating a correlation coefficient between each spectral index and an actual nitrogen content of a crop. Different central wavelengths, recalculated by using the successive projections algorithm (SPA) and the SFLA, are combined and substituted into the three selected spectral indices; and then correlation coefficients between the new spectral indices and crop nitrogen contents are calculated one by one, and the combination of central wavelengths with the highest correlation coefficient is taken as an optimal central wavelength. Thereafter, linear regression is used to fit the optimized spectral index, and the optimized spectral index with a better fitting degree is selected. The multiple linear regression prediction method (MLR) is used to construct the prediction model of the crop nitrogen content, that is, the first nitrogen content prediction model is obtained. The successive projections algorithm (SPA) and the SFLA are very classic algorithms that can be used to select characteristic wavelengths, and the specific algorithm principles will not be described in detail herein.

4. Different methods are used to screen sensitive bands at different stages of a crop.

First, a sensitive band for a specific period is extracted by using a successive projections algorithm (SPA), and a characteristic band, whose correlation with the crop nitrogen content is higher, is obtained through a series of sampling and a significance test at 0.01 level, thereby obtaining the sensitive band, which greatly reduces the number of spectral bands. Alternatively, the SFLA is used to extract several sensitive bands with the highest selection probability. By using the above two methods, the data volume can be reduced and the sensitive bands for the crop nitrogen content in a specific stage can be screened out.

According to the correlation between the sensitive bands of different varieties in different growth stages and the true values of the nitrogen content, the second nitrogen content prediction model can be constructed.

5. A machine learning algorithm is used to construct the crop nitrogen content prediction model.

On the basis of Step 4, with the sensitive band obtained by using the successive projections algorithm (SPA) and the SFLA as input variables, and the actual nitrogen content of a crop in a specific stage as response variables, the prediction model of plant nitrogen content is established by using the multiple linear regression prediction method (MLR) and the partial least squares regression method (PLS). The performance of models, obtained for different sensitive bands and through different modeling methods, are evaluated according to the coefficient of determination ($R^2$) and the root mean squared error coefficient (RMSE) of the prediction equation calculated by using the SPSS, And a nitrogen content prediction model for a crop of a specific variety in a specific stage is selected finally.

6. A prediction model with the highest prediction accuracy is selected for crops of different varieties in different growth stages.

Three main models are considered: the first nitrogen content prediction model is a nitrogen content prediction model based on the optimized spectral index established in Step 3, the second nitrogen content prediction model is a nitrogen content prediction model established by using the sensitive band in Step 5, and the third nitrogen content prediction model is a nitrogen content prediction model established by using the support vector machine regression directly, which is a nonlinear model. Although modeling is simple, modeling depends on the selection of a kernel function. These three modeling methods can be considered when predicting the nitrogen content of different crops in different growth stages, and a model with the best performance under specific conditions can be selected to complete the prediction of a crop nitrogen content.

The nitrogen content prediction model of this embodiment can accurately predict the nitrogen content of various crops in a plurality of growth stages. Based on a large number of data samples, a deep learning method and a transfer learning method are used to establish corresponding inversion models for different crops in different growth stages. At present, the nitrogen content of crops such as tea, strawberries and wheat can be accurately predicted. In addition, since a time and weather conditions cannot be completely consistent during images acquisition process, and a multispectral camera is sensitive to the intensity and the angle of illumination, illumination compensation is particularly important in order to ensure the quality and stability of a multispectral image. In this embodiment, in order to reduce the influence of sunlight on the model accuracy, a solar zenith angle and azimuth compensation model is established according to the response law of crop canopy spectral bidirectional reflection characteristics. In the nitrogen content prediction model, the influence of the sunlight angle, the azimuth and so on is considered fully to reduce the influence of different lighting environments on image quality and improve the stability of acquired image quality, so that the system can stably predict the crop nitrogen content under different environmental conditions, and the detection accuracy is further improved.

Embodiment 2

In order to implement the method corresponding to Embodiment 1 to realize the corresponding functions and technical effects, a system for automatically detecting nitrogen content is provided hereinafter.

Figure 2:
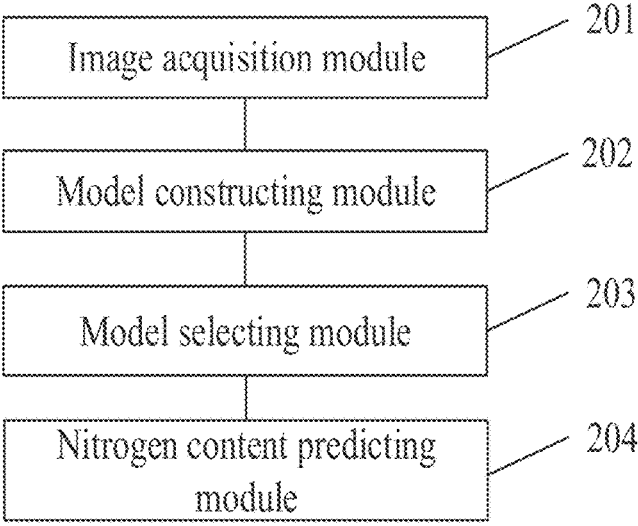
FIG. 2 is a structural diagram of a system for automatically detecting nitrogen content according to an embodiment of the present disclosure.

Referring to FIG. 2, the system includes:

an image acquisition module 201, which is configured to acquire a spectral image of a target crop;

a model constructing module 202, which is configured to construct a prediction model base;

a model selecting module 203, which is configured to select an optimal nitrogen content prediction model from the prediction model base according to a variety and a growth stage of the target crop to obtain a target model;

a nitrogen content predicting module 204, which is configured to detect, based on the spectral image of the target crop, a nitrogen content of the target crop by using the target model to obtain a predicted value of the nitrogen content of the target crop.

In one example, the model constructing module 202 includes:

a sample set acquisition unit, which is configured to acquire a sample set, where the sample set includes: spectral images of sample crops of different varieties in different growth stages and true values of nitrogen contents of the sample crops;

a first model constructing unit, which is configured to extract hyperspectral vegetation indices of the spectral images of the sample crops, and construct a first nitrogen content prediction model according to a correlation between the hyperspectral vegetation indices of different varieties in different growth stages and the true values of the nitrogen contents;

a second model constructing unit, which is configured to extract sensitive bands of spectral images of the sample crops, and construct a second nitrogen content prediction model according to a correlation between the sensitive bands of different varieties in different growth stages and the true values of the nitrogen contents; where the sensitive bands are characteristic bands whose correlation with the true values of the nitrogen contents is greater than a predetermined correlation value;

a third model constructing unit, which is configured to train a machine learning model by using the sample set to obtain a third nitrogen content prediction model;

an optimal model determining unit, which is configured to, for any variety in any growth stage, determine a model with best performance among the first nitrogen content prediction model, the second nitrogen content prediction model and the third nitrogen content prediction model as the optimal nitrogen content prediction model.

Embodiment 3

This embodiment provides an electronic device, including a memory and a processor, wherein the memory is configured to store a computer program, and the processor runs the computer program to cause the electronic device to execute the method for automatically detecting nitrogen content according to Embodiment 1.

In the embodiment, the electronic device may be a server.

In addition, the embodiment of the present disclosure further provides a non-transitory computer-readable storage medium, in which a computer program is stored, wherein the computer program, when executed by a processor, implements the method for automatically detecting nitrogen content according to Embodiment 1.

In this specification, various embodiments are described in a progressive way. The differences between each embodiment and other embodiments are highlighted, and the same and similar parts of various embodiments can be referred to each other. Since the system disclosed in the embodiment corresponds to the method disclosed in the embodiment, the system is described simply. Refer to the description of the method of the relevant points.

In the present disclosure, specific examples are applied to illustrate the principle and implementation of the present disclosure, and the explanations of the above embodiments are only used to help understand the method and core ideas of the present disclosure. At the same time, according to the idea of the present disclosure, there will be some changes in the specific implementation and application scope for those skilled in the art. To sum up, the contents of the specification should not be construed as limiting the present disclosure.

What is claimed is:

1. A method for automatically detecting nitrogen content, comprising:

acquiring a spectral image of a target crop;

selecting an optimal nitrogen content prediction model from a prediction model base according to a variety and a growth stage of the target crop to obtain a target model;

detecting, based on the spectral image of the target crop, a nitrogen content of the target crop by using the target model to obtain a predicted value of the nitrogen content of the target crop;

wherein a constructing method of the prediction model base comprises:

acquiring a sample set, wherein the sample set comprises: spectral images of sample crops of different varieties in different growth stages and true values of nitrogen contents of the sample crops;

extracting hyperspectral vegetation indices of the spectral images of the sample crops, and constructing a first nitrogen content prediction model according to a correlation between the hyperspectral vegetation indices of different varieties in different growth stages and the true values of the nitrogen contents;

extracting sensitive bands of the spectral images of the sample crops, and constructing a second nitrogen content prediction model according to a correlation between the sensitive bands of different varieties in different growth stages and the true values of the nitrogen contents; wherein the sensitive bands are characteristic bands whose correlation with the true values of the nitrogen contents is greater than a predetermined correlation value;

training a machine learning model by using the sample set to obtain a third nitrogen content prediction model;

for any variety in any growth stage, determining a model with best performance among the first nitrogen content prediction model, the second nitrogen content prediction model and the third nitrogen content prediction model as the optimal nitrogen content prediction model.

2. The method for automatically detecting nitrogen content according to claim 1, wherein the detecting, based on the spectral image of the target crop, a nitrogen content of the target crop by using the target model to obtain a predicted value of the nitrogen content of the target crop comprises:

if the target model is the first nitrogen content prediction model or the second nitrogen content prediction model, inputting the variety and the growth stage of the target crop into the target model, wherein the target model outputs the predicted value of the nitrogen content of the target crop;

if the target model is the third nitrogen content prediction model, inputting the spectral image of the target crop into the target model, wherein the target model outputs the predicted value of the nitrogen content of the target crop.

3. The method for automatically detecting nitrogen content according to claim 1, wherein the acquiring a spectral image of a target crop comprises:

determining a zenith angle and an azimuth angle at which the spectral image of the target crop is acquired under sunlight;

according to the zenith angle and the azimuth angle of the target crop, using an artificial light source to compensate for the sunlight in an environment where a multispectral camera is located;

with the compensation of the artificial light source, acquiring the spectral image of the target crop by using the multispectral camera.

4. The method for automatically detecting nitrogen content according to claim 1, wherein the acquiring a sample set comprises:

determining the zenith angle and the azimuth angle at which a spectral image of a sample crop of each variety in each growth stage is acquired under sunlight;

according to the zenith angle and the azimuth angle of the sample crop of each variety in each growth stage, using an artificial light source to compensate for the sunlight in an environment where the multispectral camera is located;

with the compensation of the artificial light source, acquiring the spectral images of the sample crops of different varieties in different growth stages by using the multispectral camera;

measuring total nitrogen contents of the sample crops by using a Kjeldahl method in a laboratory, wherein the total nitrogen contents is considered as the true values of the nitrogen contents of the sample crops.

5. The method for automatically detecting nitrogen content according to claim 1, wherein the extracting hyperspectral vegetation indices of the spectral images of the sample crops comprises:

performing preprocessing, comprising smoothing and correcting transformation, on the spectral images of the sample crops to obtain preprocessed spectral images;

determining a spectral reflectivity of each band according to the preprocessed spectral images;

performing arithmetic operation on the spectral reflectivity to obtain the hyperspectral vegetation indices; wherein the hyperspectral vegetation indices comprises a double-peak canopy nitrogen index, a normalized difference vegetation index, a modified red edge simple ratio index and a relative vegetation index.

6. The method for automatically detecting nitrogen content according to claim 1, wherein the constructing a first nitrogen content prediction model according to a correlation between the hyperspectral vegetation indices of different varieties in different growth stages and the true values of the nitrogen contents comprises:

for any variety in any growth stage, optimizing a central wavelength of each index in the hyperspectral vegetation indices by using a successive projections algorithm, and substituting an optimized central wavelength into a corresponding index calculation formula to calculate an index value;

performing a Pearson correlation test on the index value of each index in the hyperspectral vegetation indices and the true values of the nitrogen contents to obtain a correlation coefficient between each index value and the true values of the nitrogen contents;

selecting three index values with highest correlation coefficient from the hyperspectral vegetation indices as optimal spectral indices;

fitting a relationship between the optimal spectral indices and the true values of the nitrogen contents by using a multiple linear regression prediction method and/or a partial least square regression method to obtain the first nitrogen content prediction model of any variety in any growth stage.

7. The method for automatically detecting nitrogen content according to claim 1, wherein the extracting sensitive bands of the spectral images of the sample crops, and the constructing a second nitrogen content prediction model according to a correlation between the sensitive bands of different varieties in different growth stages and the true values of the nitrogen contents, comprises:

for any variety in any growth stage, extracting a sensitive band of a spectral image of a sample crop by using a random frog leaping algorithm;

fitting a relationship between the sensitive bands and the true values of the nitrogen contents by using a multiple linear regression prediction method and/or a partial least square regression method to obtain the second nitrogen content prediction model of any variety in any growth stage.

8. An electronic device, comprising a memory and a processor, wherein the memory is configured to store a computer program, and the processor runs the computer program to cause the electronic device to execute the method for automatically detecting nitrogen content according to claim 1.

9. The electronic device according to claim 8, wherein the detecting, based on the spectral image of the target crop, a nitrogen content of the target crop by using the target model to obtain a predicted value of the nitrogen content of the target crop comprises:

if the target model is the first nitrogen content prediction model or the second nitrogen content prediction model, inputting the variety and the growth stage of the target crop into the target model, wherein the target model outputs the predicted value of the nitrogen content of the target crop;

if the target model is the third nitrogen content prediction model, inputting the spectral image of the target crop into the target model, wherein the target model outputs the predicted value of the nitrogen content of the target crop.

10. The electronic device according to claim 8, wherein the acquiring a spectral image of a target crop comprises:

determining a zenith angle and an azimuth angle at which the spectral image of the target crop is acquired under sunlight;

according to the zenith angle and the azimuth angle of the target crop, using an artificial light source to compensate for the sunlight in an environment where a multispectral camera is located;

with the compensation of the artificial light source, acquiring the spectral image of the target crop by using the multispectral camera.

11. The electronic device according to claim 8, wherein the acquiring a sample set comprises:

determining the zenith angle and the azimuth angle at which a spectral image of a sample crop of each variety in each growth stage is acquired under sunlight;

according to the zenith angle and the azimuth angle of the sample crop of each variety in each growth stage, using an artificial light source to compensate for the sunlight in an environment where the multispectral camera is located;

with the compensation of the artificial light source, acquiring the spectral images of the sample crops of different varieties in different growth stages by using the multispectral camera;

measuring total nitrogen contents of the sample crops by using a Kjeldahl method in a laboratory, wherein the total nitrogen contents is considered as the true values of the nitrogen contents of the sample crops.

12. The electronic device according to claim 8, wherein the extracting hyperspectral vegetation indices of the spectral images of the sample crops comprises:

performing preprocessing, comprising smoothing and correcting transformation, on the spectral images of the sample crops to obtain preprocessed spectral images;

determining a spectral reflectivity of each band according to the preprocessed spectral images;

performing arithmetic operation on the spectral reflectivity to obtain the hyperspectral vegetation indices; wherein the hyperspectral vegetation indices comprises a double-peak canopy nitrogen index, a normalized difference vegetation index, a modified red edge simple ratio index and a relative vegetation index.

13. The electronic device according to claim 8, wherein the constructing a first nitrogen content prediction model according to a correlation between the hyperspectral vegetation indices of different varieties in different growth stages and the true values of the nitrogen contents comprises:

for any variety in any growth stage, optimizing a central wavelength of each index in the hyperspectral vegetation indices by using a successive projections algorithm, and substituting an optimized central wavelength into a corresponding index calculation formula to calculate an index value;

performing a Pearson correlation test on the index value of each index in the hyperspectral vegetation indices and the true values of the nitrogen contents to obtain a correlation coefficient between each index value and the true values of the nitrogen contents;

selecting three index values with highest correlation coefficient from the hyperspectral vegetation indices as optimal spectral indices;

fitting a relationship between the optimal spectral indices and the true values of the nitrogen contents by using a multiple linear regression prediction method and/or a partial least square regression method to obtain the first nitrogen content prediction model of any variety in any growth stage.

14. The electronic device according to claim 8, wherein the extracting sensitive bands of the spectral images of the sample crops, and the constructing a second nitrogen content prediction model according to a correlation between the sensitive bands of different varieties in different growth stages and the true values of the nitrogen contents, comprises:

for any variety in any growth stage, extracting a sensitive band of a spectral image of a sample crop by using a random frog leaping algorithm;

fitting a relationship between the sensitive bands and the true values of the nitrogen contents by using a multiple linear regression prediction method and/or a partial least square regression method to obtain the second nitrogen content prediction model of any variety in any growth stage.

15. A non-transitory computer-readable storage medium, in which a computer program is stored, wherein the computer program, when executed by a processor, implements the method for automatically detecting nitrogen content according to claim 1.

16. The non-transitory computer-readable storage medium according to claim 15, wherein the detecting, based on the spectral image of the target crop, a nitrogen content of the target crop by using the target model to obtain a predicted value of the nitrogen content of the target crop comprises:

if the target model is the first nitrogen content prediction model or the second nitrogen content prediction model, inputting the variety and the growth stage of the target crop into the target model, wherein the target model outputs the predicted value of the nitrogen content of the target crop;

if the target model is the third nitrogen content prediction model, inputting the spectral image of the target crop into the target model, wherein the target model outputs the predicted value of the nitrogen content of the target crop.

17. The non-transitory computer-readable storage medium according to claim 15, wherein the acquiring a spectral image of a target crop comprises:

determining a zenith angle and an azimuth angle at which the spectral image of the target crop is acquired under sunlight;

according to the zenith angle and the azimuth angle of the target crop, using an artificial light source to compensate for the sunlight in an environment where a multispectral camera is located;

with the compensation of the artificial light source, acquiring the spectral image of the target crop by using the multispectral camera.

18. The non-transitory computer-readable storage medium according to claim 15, wherein the acquiring a sample set comprises:

determining the zenith angle and the azimuth angle at which a spectral image of a sample crop of each variety in each growth stage is acquired under sunlight;

according to the zenith angle and the azimuth angle of the sample crop of each variety in each growth stage, using an artificial light source to compensate for the sunlight in an environment where the multispectral camera is located;

with the compensation of the artificial light source, acquiring the spectral images of the sample crops of different varieties in different growth stages by using the multispectral camera;

measuring total nitrogen contents of the sample crops by using a Kjeldahl method in a laboratory, wherein the total nitrogen contents is considered as the true values of the nitrogen contents of the sample crops.

19. The non-transitory computer-readable storage medium according to claim 15, wherein the extracting hyperspectral vegetation indices of the spectral images of the sample crops comprises:

performing preprocessing, comprising smoothing and correcting transformation, on the spectral images of the sample crops to obtain preprocessed spectral images;

determining a spectral reflectivity of each band according to the preprocessed spectral images;

performing arithmetic operation on the spectral reflectivity to obtain the hyperspectral vegetation indices;

wherein the hyperspectral vegetation indices comprises a double-peak canopy nitrogen index, a normalized difference vegetation index, a modified red edge simple ratio index and a relative vegetation index.

20. A system for automatically detecting nitrogen content, comprising:

an image acquisition module, which is configured to acquire a spectral image of a target crop;

a model selecting module, which is configured to select an optimal nitrogen content prediction model from a prediction model base according to a variety and a growth stage of the target crop to obtain a target model;

a nitrogen content predicting module, which is configured to detect, based on the spectral image of the target crop, a nitrogen content of the target crop by using the target model to obtain a predicted value of the nitrogen content of the target crop;

a model constructing module, which is configured to construct the prediction model base;

wherein the model constructing module comprises:

a sample set acquisition unit, which is configured to acquire a sample set, wherein the sample set comprises: spectral images of sample crops of different varieties in different growth stages and true values of nitrogen contents of the sample crops;

a first model constructing unit, which is configured to extract hyperspectral vegetation indices of the spectral images of the sample crops, and construct a first nitrogen content prediction model according to a correlation between the hyperspectral vegetation indices of different varieties in different growth stages and the true values of the nitrogen contents;

a second model constructing unit, which is configured to extract sensitive bands of the spectral images of the sample crops, and construct a second nitrogen content prediction model according to a correlation between the sensitive bands of different varieties in different growth stages and the true values of the nitrogen contents; wherein the sensitive bands are a characteristic bands whose correlation with the true values of the nitrogen contents is greater than a predetermined correlation value;

a third model constructing unit, which is configured to train a machine learning model by using the sample set to obtain a third nitrogen content prediction model;

an optimal model determining unit, which is configured to, for any variety in any growth stage, determine a model with best performance among the first nitrogen content prediction model, the second nitrogen content prediction model and the third nitrogen content prediction model as the optimal nitrogen content prediction model.

* * * * *